United States Patent [19]

Niewald

[11] Patent Number: 4,971,059
[45] Date of Patent: Nov. 20, 1990

[54] MEDICAL TIMING DEVICE

[76] Inventor: Jack L. Niewald, P.O. Box 224, Clinton St., Corwith, Iowa 50430

[21] Appl. No.: 99,332

[22] Filed: Sep. 18, 1987

Related U.S. Application Data

[63] Continuation of Ser. No. 890,014, Jul. 28, 1986, abandoned.

[51] Int. Cl.$^5$ ............................................. A61B 10/00
[52] U.S. Cl. ...................................... 128/630; 128/23
[58] Field of Search .................... 128/715, 687–690, 128/670, 630; 116/22 R, 24–25, DIG. 1, 44; 340/309.15; 84/484

[56] References Cited

U.S. PATENT DOCUMENTS

| | | | |
|---|---|---|---|
| 1,929,019 | 10/1933 | Ehn | 116/25 R |
| 2,468,483 | 4/1949 | Chambers et al. | 116/22 R |
| 2,893,344 | 7/1959 | Meyers | 116/DIG. 44 |
| 3,271,670 | 9/1966 | Esakov et al. | 84/484 X |
| 3,675,243 | 7/1972 | Landuyt | 84/484 X |
| 3,901,121 | 8/1975 | Kleiner | 84/484 |
| 4,377,727 | 3/1983 | Schwalbach | 128/715 |
| 4,437,381 | 3/1984 | Chen | 84/484 |
| 4,491,423 | 1/1985 | Cohen | 340/309.15 |
| 4,576,178 | 3/1986 | Johnson | 128/670 |
| 4,597,030 | 6/1986 | Brody et al. | 128/20 |
| 4,618,986 | 10/1986 | Hower | 128/715 X |

FOREIGN PATENT DOCUMENTS 0718855  3/1942  Fed. Rep. of Germany ...... 128/715

Primary Examiner—William E. Kamm
Attorney, Agent, or Firm—Zarley, Mckee, Thomte, Voorhees & Sease

[57] ABSTRACT

A means and method for medical timing of human vital signs including the steps of generating a repeating preselected time interval signal which is used to produce a sensory stimulating signal. The sensory stimulating signal is used as a reference when measuring human vital signs. The apparatus of the invention includes a housing containing a timing mechanism for producing the repeating pre-selected time interval signal and a mechanism for producing the sensory stimulating signal. The device is adapted to be used with a power source such as a battery and is small, portable, and easily maneuverable. An illuminating light is optionally includable to assist in viewing the patient and obtaining other medically related signs and readings.

18 Claims, 1 Drawing Sheet

MEDICAL TIMING DEVICE

This is a continuation of copending application Ser. No. 890,014 filed on Jul. 28, 1986, now abandoned.

BACKGROUND OF THE INVENTION

1. Field of the Invention

This invention relates to medical timing devices, and in particular, to medical timing devices which do not require reading or monitoring of a watch.

2. Problems in the Art

Current conventional methods of measuring vital signs such as pulse and respirations, or administrating such medical techniques as cardiopulmonary resuscitation (CPR) depend on accurate timing intervals. Typically the medical personnel use a watch or a clock, or a timer built into medical apparatus to produce the timing interval.

There are times when referencing a watch, clock, or other such timing device is difficult, if not impossible. In cases of darkness, or when medical personnel are working on a patient alone, exact measurement of the medically related time intervals is uncertain. Additionally, the patent could be in such a position that it is difficult or impossible for the medical personnel to reference a wrist watch or a clock. At accident scenes, medical personnel are many times dealing with life and death and the few moments required to reference such things as watches or clocks could beneficially be eliminated.

In emergency situations, it would also be many times advantageous to have a continuous reference signal. This would avoid having to recheck or restart conventional watches, clocks, or timing devices. It is also advantageous if the device is small, portable, and easily maneuverable.

Conventional timing devices also are not generally useable by persons impaired with blindness. A timing device which would give a sensory stimulating signal could be used by visually handicapped persons, the hearing impaired, or persons in emergency situations.

It is therefore a primary object of the invention to improve over or solve the problems and deficiencies in the art.

Another object of the invention is to provide a means and method of medical timing which produces a sensory stimulating signal at repeating pre-selected time intervals. A further object of the invention is to provide a means and method for medical timing which is portable, compact, and easily maneuverable.

A further object of the invention is to provide a means and method of medical timing which generates a sensory stimulating signal for use in measuring and monitoring human vital signs such as pulse and respiration.

These and other objects, features, and advantages of the invention will become apparent with reference to the accompanying specification and claims.

SUMMARY OF THE INVENTION

The present invention utilizes a small, compact, portable housing which is adaptable to hold a power source such as a battery. A timing means produces a repeating pre-selected time interval signal which is used by a sensory stimulating signal means to signal medical personnel at the end of each time interval.

The sensory stimulating signal means can be visual, audible, or tactile, or any combination of the same. By generating the repeating pre-selected time interval in this form, the medical personnel can simply refer to the signal while measuring or monitoring human vital signs without having to reference, remember, and recheck conventional timing devices such as watches or clocks. Its repeating feature also allows continuous or interrupted monitoring.

The combination of features of the invention make it particularly suitable for use in emergency medical situations. Its timing circuitry can be calibrated and adjusted to ensure accuracy. Time intervals such as 15 seconds are preferred to allow easy conversion of vital sign measurements into rate per minute.

An illuminating light can be easily incorporated into the invention to allow illumination of selected areas and to assist in the measuring or monitoring of other medical indicators such as pupil dilation, ears, nose, throat, and the like.

DETAILED DESCRIPTION OF THE PREFERRED EMBODIMENT

Figure 1:
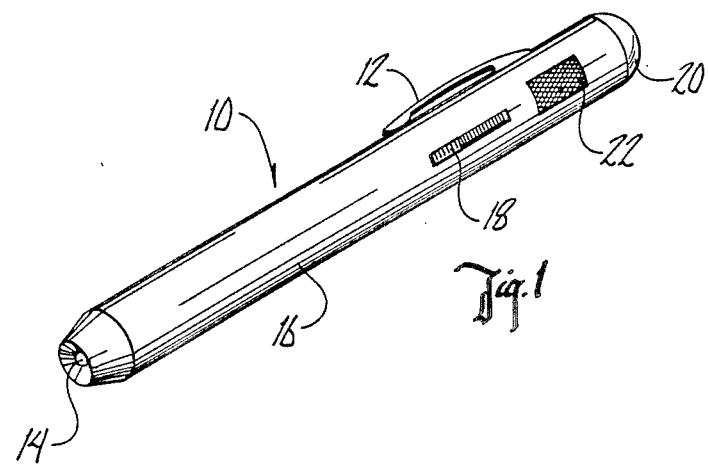
FIG. 1 is a perspective view of one embodiment of the invention.

In reference to the drawings, and in particularly FIG. 1, there is shown a medical timing device 10, in accordance with the invention. This preferably pocket size, self-contained device can be the size of a pen and include a pocket clip 12. The device can also include a penlight 14 which is powered by a battery contained within the housing 16.

A switch 18 controls operation of the unit. Switch 18 can be configured so as to operate indicator light 20 and beeper 22, or penlight 14, or both. It is even contemplated that switch 18 may operate either indicator light 20 or beeper 22 with or without penlight 14. Such is a matter of design well within those of ordinary skill in the art.

By enabling indicator light 20 or beeper 22, it is meant that electronic circuitry within housing 17 would intermittently flash indicator light 20 and/or beep beeper 22 at the end of pre-selected time intervals. Medical personnel using the invention 10 could therefore visually or audibly know the beginning and end of the time intervals needed when measuring or monitoring human vital signs. The invention 10 could be placed in the most convenient position for use and is easily repositioned, maneuvered, or picked up. The indicator light 20 and beeper 22 therefore produce a sensory stimulating signal useful for medical timing purposes.

Movement of switch 18 to enable indicator light 20 and beeper 22 begins the timing and signaling operation. Return of switch 18 to the off position ceases such operation.

Figure 2:
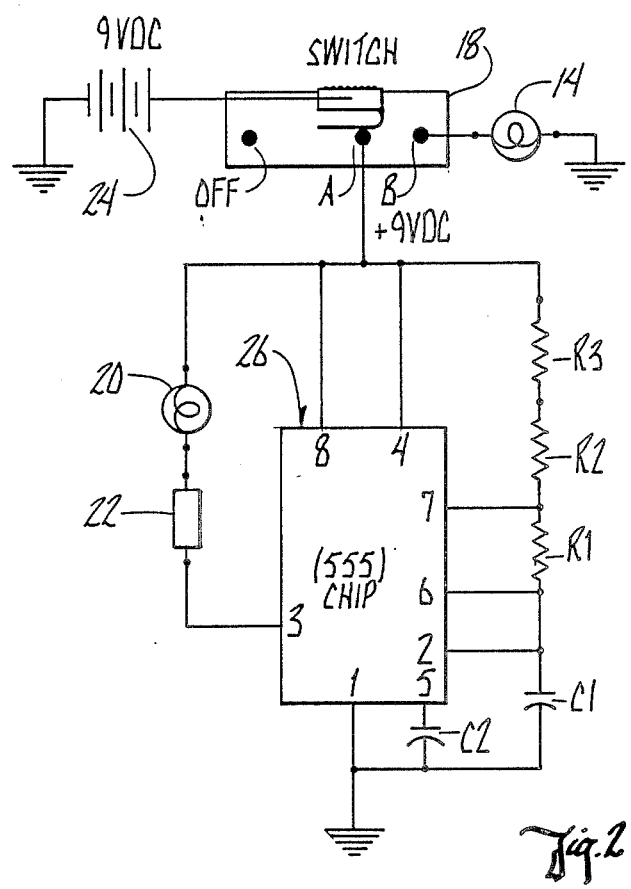
FIG. 2 is a schematic of one embodiment of electrical circuitry which can be used for the invention.

In reference to FIG. 2, a preferred embodiment of the electronics of the invention is shown. The power source can be a battery 24 such as 9 volts DC. As is depicted, switch 18 can either turn only the timing circuitry on, or only penlight 14 on, or can operate both.

The timing means for producing the repeating, pre-selected time interval signals is integrated circuit 26. Integrated circuit 26 can be what is known as a "555" chip which is widely known in the art and is available from various electronic dealers and distributors. Integrated circuit 26 is powered by battery 24 and produces an electrical signal at the end of a pre-scheduled, programmed time interval which is built-in to integrated circuit 26. Any time interval can be programmed into integrated circuit 26.

Capacitors C1 and C2, and resistors R1, R2, and R3, are connected with integrated circuit 26 to determine the exact time interval it will produce. This configuration is known and within the skill of those with ordinary skill in the art. Capacitor C1 in the preferred embodiment is a 100 microfarad (mF) 50 volt DC capacitor, whereas capicitor C2 is rated at 0.01 microfarads. Resistor R1 is 47 ohms whereas resistor R2 is 220 kilo-ohms. Resistor R3 is 10 kilo-ohms.

Resistor R3 can be substituted by a tuneable resistor which would allow fine tuning of the ultimate time interval produced and sent to generate the sensory stimulating signals.

As shown in FIG. 2, indicator light 20 and beeper 22 can be connected in series so that upon movement of switch 18 from "off" to position "A", both indicator light 20 and beeper 22 would operate at the end of each time interval. As is obvious, indicator light 20 and beeper light 22 could also be connected in parallel. It is also to be understood that it is well within the skill of the art to allow selection between use of indicator light 20 and beeper 22.

It is also noted that switch 18 is configured so that it can be moved from "off" to either position "A", wherein the timing circuitry would function, or individually to position "B" where just penlight 14 would operate. Also, switch 18 could connect both terminal "A" and terminal "B" to battery 24 to allow simultaneous operation of the timing circuitry and penlight 14.

It is to be understood that the above is a description of the preferred embodiment of the invention only, and that variations obvious to those skilled in the art are to be included. The invention is defined by the claims which follow and is not limited by the description recited above.

It can be seen the invention achieves at least all of its stated objectives.

What is claimed is:

1. In a method of emergency medical timing of a medical event such as human pulse, human respiration, and cardiopulmonary resuscitation intervals, by generating a time interval signal and producing a sensory stimulating signal from the time interval signal for reference when measuring the medical event, the improvement comprising:
   providing said time interval signal, from a portable means other than utilized to monitor the medical event, to operate at precise repeating pre-selected time span intervals, the means including a self-contained power source to power the sensory stimulating signal;
   providing said sensory stimulating signal only at the end of each said precise repeating pre-selected time span interval and in a sensory form different, independent, and separated from the medical event so that the medical event can be sensorially perceived and timed with respect to the different, independent and separate sensorially perceived time interval to allow emergency treatment and observation without the need for visually monitoring a conventional time clock, and without interruption and confusion relating to a variety of visual or audible cues and signals; and
   producing a light beam from the power source of the portable means to illuminate selected areas and to enable the user to check other medical related items and signs such as pupil dilation, ears, nose, throat, and the like.

2. The method of claim 1 wherein the repeating pre-selected time intervals signal is for 15 seconds to allow reference for measuring human pulse, respiration, cardiopulmonary resuscitation, and other medical related events.

3. The method of claim 1 wherein the sensory stimulating signal is audible.

4. The method of claim 1 wherein the sensory stimulating signal is visual.

5. The method of claim 1 wherein the sensory stimulating signal is tactile.

6. The method of claim 1 wherein the sensory stimulating signal is audible and visual.

7. The method of claim 1 wherein the repeating pre-selected time interval signal and the sensory stimulating signal are produced in a housing which is small, portable, and easily maneuverable.

8. An emergency medical timing device for emitting a sensory stimulating signal at pre-selected time intervals for monitoring a medical event such as human pulse, human respiration, or cardiopulmonary resuscitation, comprising:
   a housing containing a self-contained power source;
   said housing being separate from any means utilized to monitor the medical event, self-contained, portable, transportable on a user and capable of being held and operated in a user's hand;
   a time span timing means powered by said power source for producing a precise repeating pre-selected time span interval signal;
   a sensory stimulating signal means powered by the power source operatively associated with the housing and the time span timing means for producing a sensory stimulating signal only at the end of each precise repeating pre-selected time span interval for reference when measuring the medical event, said sensory stimulating signal being in a sensory form different, independent, and separated from the medical event so that the medical event can be sensorially perceived and timed with respect to the separate, different, and independently sensorially perceived time interval to allow emergency treatment and observation without the need for visually monitoring a conventional time clock, and without interruption and confusion relating to a variety of visual or audible cues and signals;
   whereby said pre-selected time interval signal may be set without synchronization to said medical event being measured; and
   an illuminating light means powered by the power source to illuminate selected areas and assist in other medically related checks such as pupil dilation, ears, nose, throat, and the like.

9. The device of claim 8 wherein the power source is a battery means.

10. The device of claim 8 wherein the timing means is an electrical circuit.

11. The device of claim 10 wherein the timing means is an integrated circuit.

12. The device of claim 11 wherein the timing means includes a tuneable resistor in association with the integrated circuit to insure accuracy of the time interval signal.

13. The device of claim 8 wherein the sensory stimulating signal is audible.

14. The device of claim 8 wherein the sensory stimulating signal is visual.

15. The device of claim 8 wherein the sensory stimulating signal is tactile.

16. The device of claim 8 wherein the sensory stimulating signal is audible and visual.

17. The device of claim 8 wherein the time interval signal is 15 seconds for use in taking pulse, respiration, cardiopulmonary resuscitation, and other medical events.

18. The device of claim 8 further comprising an on/off switch means between the power source and the timing means, operation of the on/off switch means beginning the repeating pre-selected time interval signal.

* * * * *